(12) United States Patent
Szommer

(10) Patent No.: US 7,871,199 B2
(45) Date of Patent: Jan. 18, 2011

(54) DENTAL X-RAY BITE BLOCK AND ALIGNMENT METHOD

(75) Inventor: Tanya Lisbet Szommer, 5305 Swiftcurrent Tran, Mississauga, Ontario (CA) L5R 2J3

(73) Assignee: Tanya Lisbet Szommer, Mississauga, Ontario (CA)

( * ) Notice: Subject to any disclaimer, the term of this patent is extended or adjusted under 35 U.S.C. 154(b) by 0 days.

(21) Appl. No.: 12/220,324

(22) Filed: Jul. 24, 2008

(65) Prior Publication Data
US 2009/0168953 A1    Jul. 2, 2009

Related U.S. Application Data

(60) Provisional application No. 61/018,308, filed on Dec. 31, 2007.

(51) Int. Cl.
*A61B 6/14* (2006.01)
(52) U.S. Cl. ................... 378/170; 378/191
(58) Field of Classification Search ............. 378/191, 378/168, 170; D24/161
See application file for complete search history.

(56) References Cited

U.S. PATENT DOCUMENTS

| | | | | |
|---|---|---|---|---|
| 2,035,051 A | * | 3/1936 | Daly | 378/170 |
| 2,245,395 A | * | 6/1941 | Goldberg | 378/170 |
| 2,899,058 A | * | 8/1959 | Maurer | 209/172.5 |
| 3,473,026 A | * | 10/1969 | Updegrave | 378/170 |
| 4,048,506 A | * | 9/1977 | Updegrave | 378/170 |
| 4,295,050 A | * | 10/1981 | Linden | 378/205 |
| 4,554,676 A | * | 11/1985 | Maldonado et al. | 378/170 |
| 4,606,063 A | * | 8/1986 | Berghagen | 378/41 |
| 4,874,884 A | * | 10/1989 | McKinney et al. | 558/338 |
| 5,090,047 A | * | 2/1992 | Angotti et al. | 378/170 |
| 5,256,982 A | * | 10/1993 | Willis | 378/168 |
| 5,799,058 A | * | 8/1998 | Willis et al. | 378/168 |
| 6,520,676 B1 | * | 2/2003 | Schmitz | 378/191 |
| 6,592,256 B2 | * | 7/2003 | Da Rold et al. | 378/168 |
| 6,652,141 B1 | * | 11/2003 | Cianciosi | 378/191 |
| 7,056,015 B2 | * | 6/2006 | Diederich | 378/170 |

* cited by examiner

*Primary Examiner*—Edward J Glick
*Assistant Examiner*—Thomas R Artman

(57) ABSTRACT

A bitewing x-ray film holder for interproximal radiographic analysis. The device includes a bite block including a biting portion, a dental medium holder for placement of a dental x-ray imaging medium, and an alignment guide extending along the biting portion to aid a dental professional in achieving a perpendicular or near perpendicular relationship of the x-ray medium to the interproximal region of clenched maxilliary and mandibular teeth. The bite block also includes a textured portion extending substantially adjacent to the alignment guide to provide friction between the biting surfaces of the teeth and the bite block.

20 Claims, 7 Drawing Sheets

DENTAL X-RAY BITE BLOCK AND ALIGNMENT METHOD

This invention relates generally to the field of an improved dental positioning apparatus and method of use for taking of bitewing radiographs which allows for the placement of the dental x-ray medium perpendicular or near perpendicular to the interproximal surfaces of teeth, thereby minimizing distortion and improper focus. This application claims priority under 35 U.S.C. §119(e) from provisional application Ser. No. 61/018,308, filed Dec. 31, 2007.

FIELD OF THE INVENTION

Background of the Invention

Bitewing x-rays are an integral aspect of ongoing dental patient care. They have a host of uses including the diagnosis of interproximal caries and incipient lesions, location of subgingival calculus, the documentation of existing treatment and any other normal or abnormal pathology, amidst other things. Today dental professionals have a choice of dental x-ray mediums including x-ray sensitive films or an x-ray sensitive image sensor (digital). In both cases, a bite block or a bite tab is often used to attempt to align the x-ray collimator apparatus with the interproximal surfaces of the teeth.

However, it is very difficult with existing bite block or bite tab apparatus to precisely align the x-ray collimator at right angles to the interproximal surfaces of radiographic interest, thereby necessitating the exposure by the patient to additional radiation as re-takes are often required.

Therefore, a need exists for a bitewing holder permitting the dental professional to securely place the dental x-ray medium perpendicular or near perpendicular to the interproximal surfaces being radiographically examined by providing a visible and tangible marker which may be adjusted to accommodate the positioning needs of individual patients.

SUMMARY OF THE INVENTION

An improved bitewing x-ray film holder for interproximal radiographic analysis and method for use is provided.

A bite block for taking bitewing x-rays on a dental x-ray medium is provided comprising an alignment guide on a biting portion of the bite block. The alignment guide extends at least part of the way between a handle portion and a dental medium holder portion of the bite block, whereby the alignment guide can be substantially aligned parallel to interproximal surfaces of interest of meeting maxillary and mandibular buccal surfaces upon insertion into an oral cavity of a patient, thereby positioning the dental x-ray medium perpendicular or near perpendicular to the interproximal surfaces of interest.

The alignment guide may further comprise a flat topped section where at least a portion of the flat topped section is elevated relative to the biting portion of the bite block.

The bite block may also comprise two alignment guides, one of which is placed on a front portion and the other of which is placed on a rear portion of the bite block, thereby enabling the bite block to be used on both sides of the patient's oral cavity by reversing the bite block.

The alignment guide may also differ in appearance from the remainder of the biting portion of the bite block (including differing in color from a remainder of the biting portion of the bite block).

The bite block may further comprise a plurality of elevated, transverse ridges extending substantially adjacent to and parallel to the alignment guide, said ridges assisting in holding of maxillary and mandibular teeth when the patient is biting on the bite block.

The bite block may also comprise openings on the dental medium holder on one or both sides of the bite block.

A portion of the bite block substantially adjacent to the dental medium holder may also be of a greater width than a width of the bite block substantially adjacent to the handle portion of the bite block.

A method of taking bitewing x-rays on a dental x-ray medium is also provided comprising the steps of: placing a bite block which comprises an alignment guide on a biting portion of the bite block into an oral cavity of a patient, said alignment guide extending at least part of the way between a handle portion and a dental medium holder portion of the bite block, said dental medium holder containing mounted unexposed dental medium which medium is placed adjacent to an area of radiographic interest; having the patient bite down on the biting portion of the bite block; while the patient is biting on the biting portion, aligning the alignment guide substantially parallel to interproximal surfaces of interest of meeting mandibular and maxillary buccal surfaces; and exposing the dental x-ray medium by emitting x-ray beams.

The method may also further comprise the steps of sliding an aiming ring along a guide rod adjacent to a patient's cheek, said guide rod connected to the handle portion of the bite block and said aiming ring slideably mounted on the guide rod; and positioning an x-ray collimator tube parallel and adjacent to the aiming ring prior to exposing the dental x-ray medium by emitting x-ray beams but after aligning the alignment guide.

The method may also comprise two alignment guides, one of which is placed on a front portion and the other of which is placed on a rear portion of the bite block, thereby enabling the bite block to be used on both sides of the patient's oral cavity by reversing the bite block in the patient's mouth.

The method may also comprise an alignment guide differing in color from a remainder of the biting portion of the bite block and also optionally the bite block may further comprise a plurality of elevated, transverse ridges extending substantially adjacent to and parallel to the alignment guide, said ridges assisting in holding of maxillary and mandibular teeth when the patient is biting on the bite block.

The method may also comprise the step of aligning the alignment guide with pre-molars and molars of a patient.

BRIEF DESCRIPTION OF THE DRAWINGS

The invention may be further understood with reference to the following drawings which illustrate but do not limit the invention described therein.

DETAILED DESCRIPTION OF DRAWINGS

Figure 1:
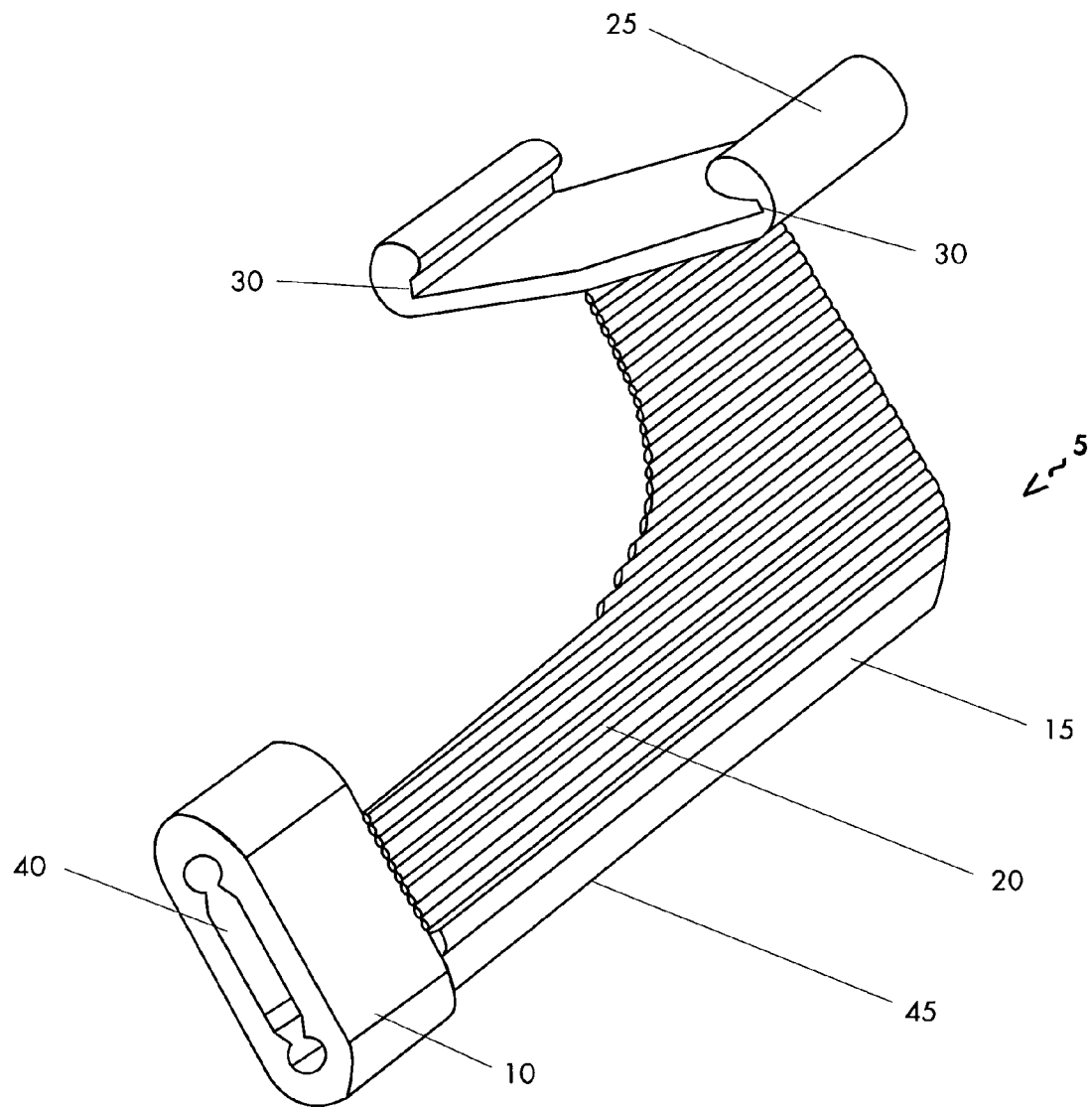
FIG. 1 is a top perspective view of a dental x-ray bite block.

With reference to FIG. 1, a bite block (5) is depicted which has a handle (10). The bite block (5) has an alignment guide (15) on an upper and lower side of a biting portion (45) of the bite block (5). The alignment guide (15) preferably runs substantially down a length of a biting portion of the bite block (5) and is preferably of a contrasting colour to the rest of the bite block (5), thereby enabling a dental professional to quickly identify the alignment guide (15). Preferably, there are also a plurality of transverse ridges (20) adjacent to the alignment guide (15) which assist in the holding of the maxilliary and mandibular teeth when the bite block (5) is inserted into a patient's oral cavity. The transverse ridges (20) are preferably a plurality of raised ribbed ridges for securely holding the bite block (5) once it has been intra-orally positioned. The alignment guide (15) comprises a flat-topped section which is elevated relative to the transverse ridges (20) but does not exceed the height of a tooth crown such that it will not significantly interfere with an exposed radiographic image.

The bite block (5) is preferably composed of polyethylene (a thermoplastic) having a flow rate of between 40 and 80, and more preferably 60, such that the bite block (5) may be economically produced and therefore designed for a single use. However, it is understood that the bite block (5) may consist of any type of material that is suitable for introduction into the oral cavity of a patient provided that x-rays can pass substantially without distortion through the bite block (5). In the case of a re-usable bite block, it is understood that the bite block (5) would be comprised of a polyethylene with a higher flow rate such that it can be safely sterilized via an autoclave.

A dental medium holder (25) is provided for insertion of a desired x-ray medium (including film or digital). Metal guide rod receiving slots (40) are provided on the handle (10) for insertion of a metal guiding rod (35) (depicted in FIG. 6).

Figure 2:
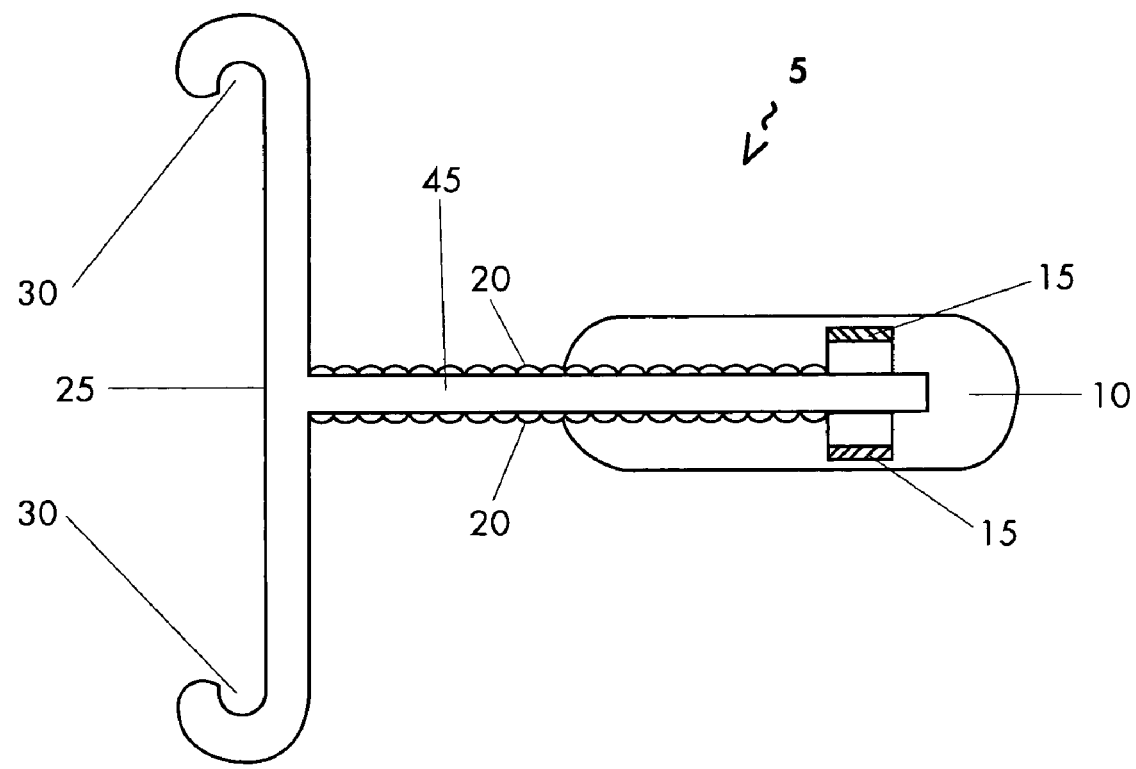
FIG. 2 is a front view thereof.
Figure 3:
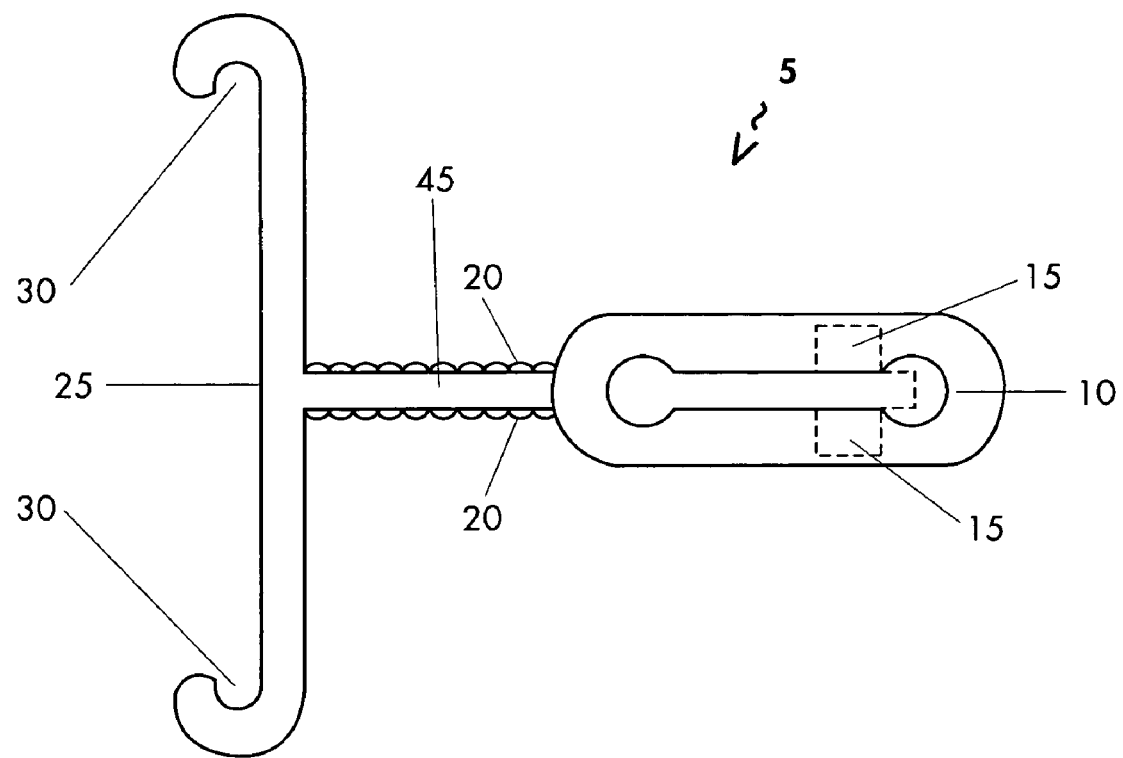
FIG. 3 is a rear view thereof.
Figure 4:
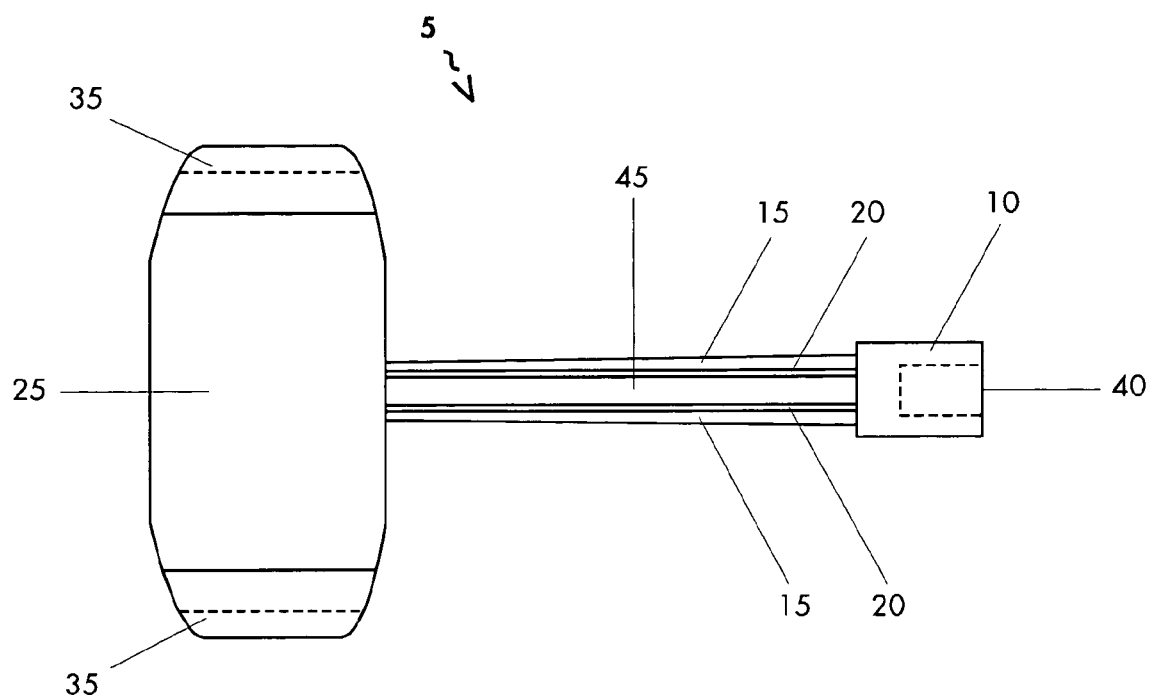
FIG. 4 is a left side view thereof.
Figure 5:
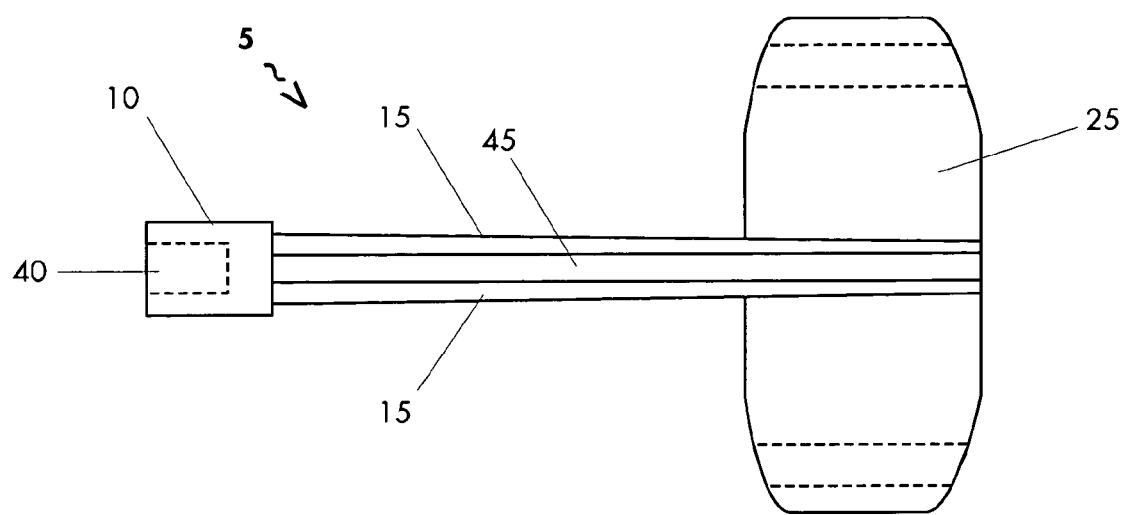
FIG. 5 is a right side view thereof.
Figure 5A:
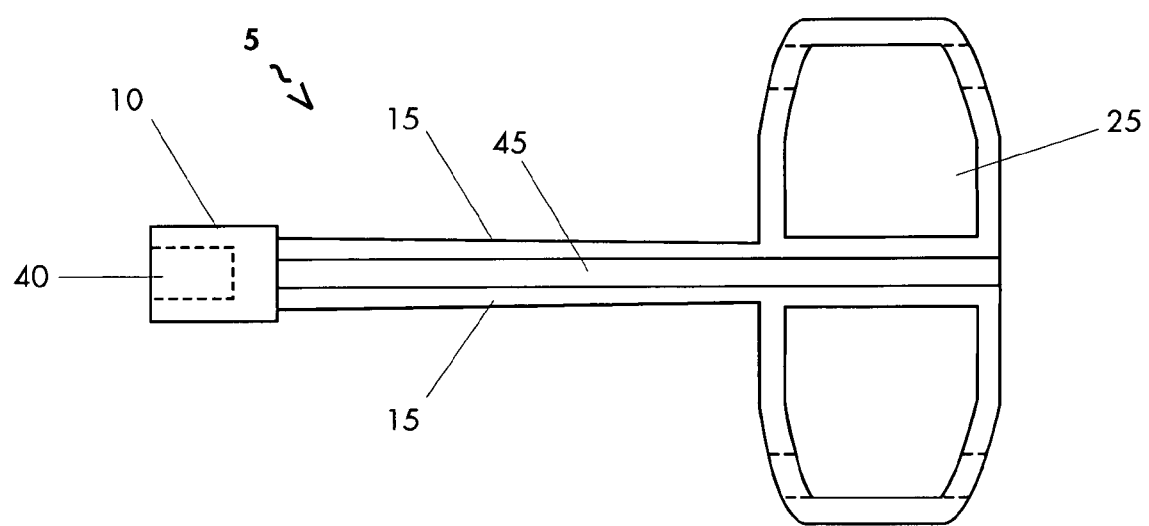
FIG. 5A is a right side view of an alternate embodiment.

Turning to FIGS. 2 and 3, in a preferred embodiment, the bite block (5) generally has a T-shaped appearance and the dental medium holder (25) has a horizontal rectangular shape and is of uniform thickness. However, the dental medium holder (25) can be adapted by the addition of one or more openings or cut-outs. The bite block (5) slants downward and inward to a proximal end and attaches to a mid-region of the dental medium holder (25) on both sides of the bite block (5), thereby reducing open bite and minimizing distortion of the exposed x-ray medium. In one embodiment and as illustrated in FIG. 5A, an opening in the dental medium holder (25) is provided on either side of the mid-region of the dental of the dental medium holder (25). The bite block (5) is generally perpendicular to the dental medium holder (25) and the handle (10). Dental medium receiving slots (30) are provided in the dental medium holder (25) for insertion of a dental medium (65) such as a film or digital packet.

Figure 6:
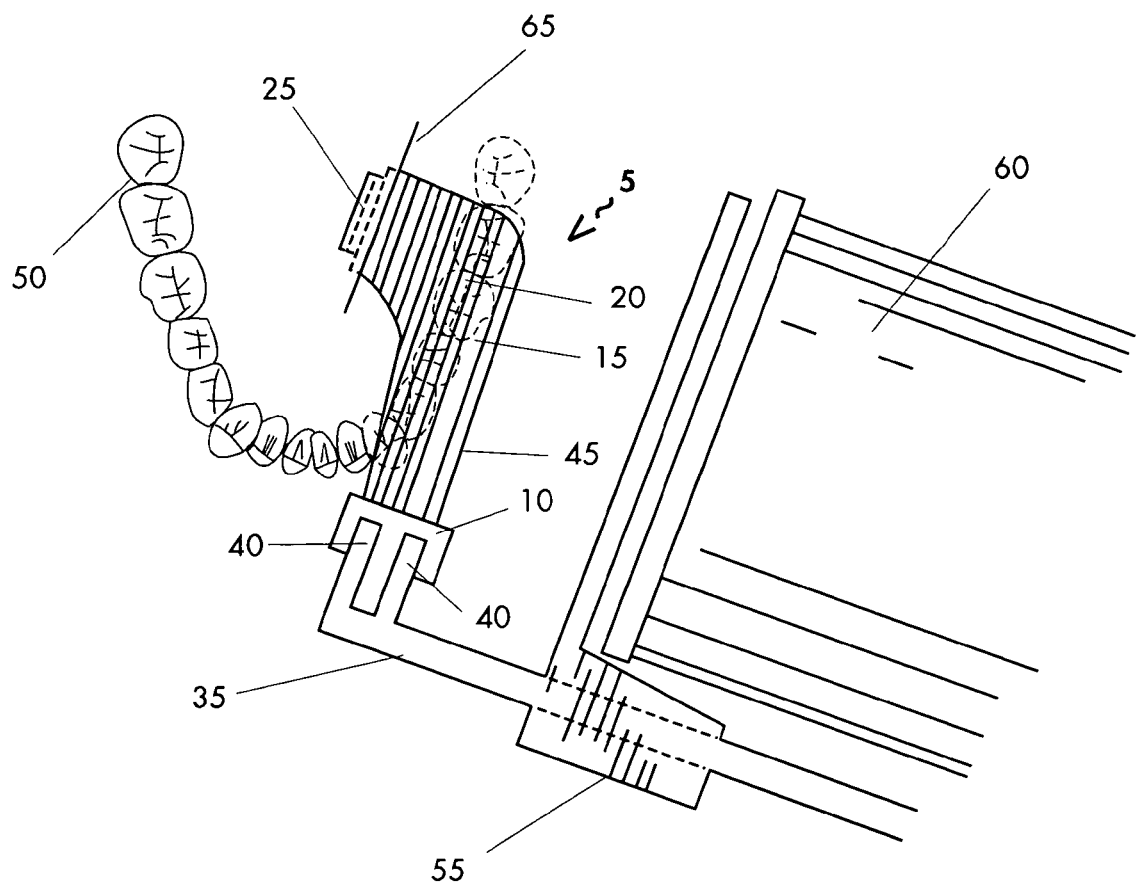
FIG. 6 is a top plan view of the dental x-ray bite block holder positioned on the teeth for taking a bite-wing x-ray, adjacent to an x-ray collimator tube.

Turning to FIG. 6, the bite block (5) is depicted in operation. The bite block (5) with mounted film in the dental medium holder (25) is placed in a posterior of an intra-oral cavity of a patient while the handle (10) and part of the bite block (5) extend outwardly from a patient's jaw and between a patient's lips. When orientated in the patient's mouth, the bite block (5) is generally parallel with the occlusal surfaces of the teeth and the dental medium holder (25) is generally perpendicular to the interproximal region of the clenched maxilliary and mandibular teeth. At a proximal end of the metal guiding rod (35) is a conventional aiming ring (55) which is positioned adjacent to a cheek of the patient. A collimator tube (60) is positioned generally parallel to the aiming ring (55).

In operation, a clinician intra-orally places the bite block (5) into the posterior of the mandible (5), orienting the dental medium holder (25) with mounted unexposed dental medium (65) adjacent to the teeth of radiographic interest. The body of the bite block (5) is superior to the occlusal surfaces of the teeth of the mandible (50). The clinician then instructs the patient to slowly bite along the bite block (5) and on the plurality of transverse ridges (20). While the patient is biting, the clinician aligns the alignment guide (15) parallel to the meeting maxillary and mandibular buccal surfaces and instructs the patient to maintain a firm bite upon the bite block (5). The clinician then ensures that the alignment guide (15) is aligned with meeting pre-molars and molars in the patient's mouth (and if not, then the patient is instructed to release the bite block (5) and bite down on the bite block (5) again or if only a slight adjustment is necessary, the clinician may adjust the bite block (5) while the patient is biting until the alignment guide (15) is aligned with the meeting pre-molars and molars). The clinician then slides the aiming ring (55) along the metal guiding rod (35) and positions the collimator tube (60) parallel and adjacent to the aiming ring (55). The patient is instructed to continually and firmly bite upon the bite block (5) while the clinician exits the operatory and exposes the mounted film by emitting the x-ray beams. The bite block (5) and exposed mounted film are then removed and processed. If necessary, the bite block (5) may be mounted with another unexposed film and inverted (flipped) to accommodate radiographic exposure of teeth of the opposite side of the arch of the patient's mouth.

It is to be expressly understood that there are a number of modifications that may be made to the overall design which would still be within the scope of this invention. For illustrative purposes only, the number of transverse ridges (20) may be varied, the alignment guide (15) can vary in appearance and the bite block (5) can also be manufactured in various sizes to accommodate films of different sizes (that are used in different sized mouths). One skilled in the art would realize that there are numerous modifications that could be made which are still within the scope of this invention.

The above description is intended in an illustrative rather than restrictive sense. Variations may be apparent to those skilled in the art without departing from the spirit and scope of the invention as defined by the claims set out below.

What is claimed is:

1. A bite block for taking bitewing x-rays on a dental x-ray medium comprising:
   a biting portion having a longitudinal axis extending from a handle portion to a dental medium holder portion of the bite block;
   an alignment guide extending along the biting portion of the bite block at least part of the way between the handle portion and the dental medium holder portion of the bite block so that the longitudinal axis of the alignment guide is parallel to the longitudinal axis of the biting portion so that the longitudinal axis of the alignment guide likewise extends from the handle portion to the dental medium holder portion, the alignment guide being configured to be aligned substantially parallel to interproximal surfaces of interest of meeting maxillary and mandibular buccal surfaces upon insertion into an oral cavity of a patient, thereby positioning a dental x-ray medium perpendicular or near perpendicular to the interproximal surfaces of interest; and
   a textured portion extending substantially adjacent to the alignment guide, whereby the textured portion provides for friction between biting surfaces of the maxillary and mandibular teeth and the biting portion of the bite block.

2. The bite block of claim 1 wherein the alignment guide includes a flat topped section having at least a portion thereof elevated relative to the biting portion of the bite block.

3. The bite block of claim 1 further comprising two alignment guides, one of which is placed on a front portion and the other of which is placed on a rear portion of the bite block, thereby enabling the bite block to be used on both sides of the patient's oral cavity.

4. The bite block of claim 1 wherein the alignment guide differs in appearance from the remainder of the biting portion of the bite block.

5. The bite block of claim 4 wherein the alignment guide differs in color from a remainder of the biting portion of the bite block.

6. The bite block of claim 1 further comprising a plurality of elevated, transverse ridges extending substantially adjacent to and parallel to the alignment guide, the ridges assisting in holding maxillary and mandibular teeth when the patient is biting on the bite block.

7. The bite block of claim 1 wherein the alignment guide is aligned with pre-molars and molars of the patient.

8. The bite block of claim 1 wherein the bite block is made from polyethylene.

9. The bite block of claim 1 wherein the dental x-ray medium is selected from the group consisting of x-ray sensitive films and x-ray sensitive digital image sensors.

10. The bite block of claim 1 wherein the dental x-ray medium is held either vertically or horizontally relative to the dental medium holder.

11. The bite block of claim 1 wherein the dental medium holder includes openings on one or both sides of the bite block.

12. The bite block of claim 1 wherein a portion of the bite block substantially adjacent to the dental medium holder is of a greater width than a width of the bite block substantially adjacent to the handle portion of the bite block.

13. A method of taking bitewing x-rays on a dental x-ray medium comprising the steps of:
 a. placing a bite block, which comprises a biting portion having a longitudinal axis extending from a handle portion to a dental medium holder portion of the bite block and an alignment guide extending along the biting portion of the bite block at least part of the way between the handle portion and the dental medium holder portion of the bite block so that the longitudinal axis of the alignment guide is parallel to the longitudinal axis of the biting portion so that the longitudinal axis of the alignment guide likewise extends from the handle portion to the dental medium holder portion, into an oral cavity of a patient, the dental medium holder containing mounted unexposed dental medium which medium being placed adjacent to an area of radiographic interest;
 b. having the patient bite down on the biting portion of the bite block such that the bite block is moveable between mandibular and maxillary buccal surfaces of the area of radiographic interest;
 c. while the patient is biting on the biting portion, aligning the alignment guide substantially parallel to interproximal surfaces of interest of meeting mandibular and maxillary buccal surfaces;
 d. once the alignment guide is aligned, having the patient apply a firm bite upon the bite block to hold the bite block in place and
 e. exposing the dental x-ray medium by emitting x-ray beams.

14. The method of claim 13 further comprising the steps of:
 f. sliding an aiming ring along a guide rod adjacent to a patient's cheek, said guide rod connected to the handle portion of the bite block and said aiming ring slideably mounted on the guide rod; and
 g. positioning an x-ray collimator tube parallel and adjacent to the aiming ring prior to exposing the dental x-ray medium by emitting x-ray beams but after aligning the alignment guide.

15. The method of claim 13 wherein the alignment guide includes a flat topped section having at least a portion thereof elevated relative to the biting portion of the bite block.

16. The method of claim 13 wherein the bite block includes two alignment guides, one of which is placed on a front portion and the other of which is placed on a rear portion of the bite block, thereby enabling the bite block to be used on both sides of the patient's oral cavity.

17. The method of claim 13 wherein the alignment guide differs in color from a remainder of the biting portion of the bite block.

18. The method of claim 13 wherein the bite block further comprises a plurality of elevated, transverse ridges extending substantially adjacent to and parallel to the alignment guide, said ridges assisting in holding of maxillary and mandibular teeth when the patient is biting on the bite block.

19. The method of claim 13 wherein the alignment guide is aligned with pre-molars and molars of a patient.

20. The method of claim 13 wherein the dental x-ray medium is selected from the group consisting of x-ray sensitive films and x-ray sensitive digital image sensors.

* * * * *